United States Patent [19]

Oh et al.

[11] Patent Number: 5,162,113
[45] Date of Patent: Nov. 10, 1992

[54] ORAL COMPOSITION FOR TREATING BONE DISORDERS

[76] Inventors: Jung M. Oh, 75-04 Roosevelt Ave., Jackson Heights, N.Y. 11372; Il H. Kim, 1048-2, Juklim-ri, Kyungsangnam-do, Rep. of Korea; Jeong S. Oh, 2911 Brighton, Brooklyn, N.Y. 11235

[21] Appl. No.: 700,682

[22] Filed: May 15, 1991

[51] Int. Cl.⁵ ............................................. A61K 35/78
[52] U.S. Cl. ................................................. 424/195.1
[58] Field of Search ..................................... 424/195.1

[56] References Cited

PUBLICATIONS

King, American Dispensatory, 8th Ed., 1870, pp. 189–190.

*Primary Examiner*—John W. Rollins
*Attorney, Agent, or Firm*—Kenyon & Kenyon

[57] ABSTRACT

A method and composition for treating bone disease with an herbal medicine is disclosed. The patient is orally treated with a composition including powdered safflower seed. In a preferred embodiment, the composition also includes powdered bark of *ulmas davidiana* root. An alternative embodiment of the composition contains the aqueous extract of powdered safflower seed with or without Jookyom.

3 Claims, No Drawings

ORAL COMPOSITION FOR TREATING BONE DISORDERS

BACKGROUND OF THE INVENTION

This application relates to an orally administered composition derived from plants which is useful for treating bone disorders.

Numerous plants were once believed to have medicinal value. However, the attention of the scientific community has turned away from research in this area. While the attention paid to medical botany has decreased in recent years, the pharmacological effectiveness of certain botanical remedies remains useful, and there remains a long felt need for continued research in this area.

Numerous plants and plant derivatives are presently used for the treatment of disease. For example, mandrake (*mandragora officinarum*) yields the alkaloid hyoscine, which is a powerful analgesic. Opium, which is a dried exudate from the unripe seedpods of the opium poppy (*papaver somniferum*) contains many alkaloids, some of which have medicinal value. Morphine and codeine are used for their analgesic properties; papaverine is used to treat intestinal colic and vascular spasm, and noscapine is an antitussive.

The autumn crocus (*colchicum autumnale*) contains colchicine, which is very effective for the treatment of gout. The purple foxglove (*digitalis purpurea*) and wooly foxglove (*digitalis lanata*) contain potent produce positive inotropic effects when administered orally, and are used to treat congestive heart failure.

The composition described herein is used to treat bone disorders. Bone fractures are initially treated by traditional methods such as by resetting, splinting and immobilizing the limb, such as with a cast. Suitable casts may be made from plaster or plastics.

In cases of severe fracture, the bone may be repaired by surgically attaching a plate made of titanium alloy, stainless steel, bioglass, aluminum oxide ceramic, polyethylene, polytetrafluoroethylene, or silicone to the bone across the fracture, with screws and/or bone cement. Metal rods have also been used successfully as a means of splinting and immobilizing damaged bone.

Bone transplants have also been attempted using homologous bone, bone cells, and artificial bone, with varying degrees of success.

Prosthetic devices have also been used to replace degenerated bone.

Additionally, potentially severe bone disease such as rheumatoid and osteoarthritis, osteoporosis and the like, as well as diseases such as non-specific bone related pain has been treated by various means, ranging from the use of non-steroidal antinflammatory drugs to gold injections.

The invention described herein utilizes an oral composition as an adjunct to the conventional bone disease treatments described above. For example, when a broken bone is to be treated, the fracture is set by a physician and placed into a cast or splint. In addition to these measures, and in accordance with the present invention, the composition described herein is administered orally to reduce the pain, hasten the formation of new bone across the fracture and strengthen the pre-existing bone. This leads to increased bone density, decreased bone brittleness and reduced bone pain.

When the composition is used to treat non-fracture related bone disease, e.g., arthritis, conventional therapy is supplemented in accordance with the invention described herein.

SUMMARY OF THE INVENTION

The present invention is related to a composition for treating bone disorders which comprises powdered safflower seed.

The composition may also contain up to about 10% by weight of the bark of *ulmas davidiana* root and/or Jookyom.

In a preferred embodiment, the safflower seed is browned, powdered and then mixed with a desired amount of powdered bark of *ulmas davidiana* root or Jookyom.

The present invention also relates to methods of treating such bone disorders comprising treating the patient orally with from about 50 to about 100 grams of a composition comprised of from about 90 to about 100 percent safflower seed and from about 10 to about 0 percent bark of ulmas davidiana root, or Jookyom one to eight times a day.

DETAILED DESCRIPTION

Safflower seed has a circulatory improvement effect when administered orally in untreated form. The composition is essentially non-toxic and has a slightly bitter and sweet taste.

When safflower seed is cooked, e.g., fried, the pharmacological profile changes. It demonstrates activity as a bone-healing or bone growth stimulating composition, and improves wound healing and the like. It is noted that safflower seed contains low levels of a platinum compound as well as other natural ingredients which are useful for treating bone disorders, resulting in increased bone strength and density, decreased brittleness and reduced bone pain.

As used herein, the terms "bone disorders' and "bone disease' refer to fractures and non-fracture related conditions known to those skilled in the art, which respond therapeutically to the composition described herein.

Therapeutic responses can be measured objectively, such as through the use of x-rays, CAT scans and the like, as well as clinically, judged by a reduction in the symptoms.

It has been discovered that broken bones heal quickly and tender, weak bones are strengthened by treating the patient with the composition comprised of a mixture of safflower seed and bark of *ulmas davidiana* root and optionally Jookyom.

In a preferred embodiment of the invention, the powdered safflower seed comprises at least about 90 percent of the composition and the bark of the *ulmas davidiana* root comprises no more than about 10 percent by weight of the composition. entirely.

In the most preferred embodiment, the composition comprises about 95 safflower seed and about 5 percent bark of *ulmas davidiana* root.

The composition is typically prepared as follows. First, safflower seeds are cooked, e.g., lightly fried, until they attain a light brown color. It seems that cooking the safflower seeds prior to comminution enhances the potency of the preparation, making its bone-treating effectiveness more pronounced. Additionally, by lightly browning the seeds prior to comminution, a hematinnic effect may be observed; bruises seem to dissipate more quickly.

The browned safflower seeds are ground into a powder. The resultant powder is mixed with a desired amount of powdered bark of ulmas davidiana root, in the relative proportions recited above. Bark or *ulmas davidiana* is an analgesic agent which also has antiseptic properties. It is combined with the safflower seed described herein (up to about 10% w/w) to form a preferred composition for oral use. Preferably the bark of *ulmas davidiana* root is used, since it seems to have stronger medicinal properties than the other plant parts.

Alternatively, the safflower seeds may be boiled after grinding into a powder. This tends to extract the active components from the seed into the liquid. This is particularly suitable for making orally administered solutions. The liquid medium is administered to the patient in flavored or unflavored form. One preferred example is ginger tea containing an extract of the safflower seed, bark of ulmas davidiana root and/or Jookyom.

The patient may be treated with an oral dose of from about 50 to about 100 grams of the powdered composition once or twice a day up to as high as one dose about every 2 to 3 hours. When a liquid extract of safflower seed is administered, equivalent doses of the liquid containing the extract of safflower seed, bark of *ulmas davidiana* root and/or Jookyom should be given.

For milder cases of bone disease, adults typically take about 20-50g of the composition four times daily at mealtime and at bedtime. For more serious cases, the dose can be increased to about 100 g every 2 to 3 hours. Children may take reduced dosages based upon their age and body weight.

When the powdered composition is administered, the mixture may be tableted, encapsulated, or solubilized in a suitable liquid vehicle for the powder and dispensed as a solution or suspension. When the boiled extract is administered, it is best utilized as an herbal flavored tea.

In a preferred embodiment of the invention, the safflower seeds are cleaned, lightly fried to a golden brown and then ground into a powder. Separately wash and grind the bark of *ulmas davidiana* root and combine an amount of davidania powder up to about 10% of the total weight of the blend with an appropriate quantity of powdered safflower seed.

The powder mixture need not be combined with any diluents, and can be placed directly into a liquid and ingested in the form of a suspension or slurry.

The safflower seed powder may alternatively be combined with Jookyom in the flavored tea described above, again with an appropriate sweetener as necessary.

The preferred safflower seed is taken from plants grown in South Korea. When Korean safflower seed is used as described above, the doses described above are adequate. When other safflower seed is used, the doses may be increased.

Generally, improvement in the bone disease condition is apparent within about one week to ten days after the start of treatment. Serious fractures and patients who have difficulty healing can be treated for about 20 to about 60 days, and patients with osteoporosis can be treated at reduced doses using a maintenance regimen, e.g., regular doses for longer than about 3 months.

In one instance, the composition described herein was used to treat an 18 year old male patient who was hospitalized with a neck fracture (C4-C6) which occurred in an automobile accident. After conventional treatment by a physician, the patient's medical care was supplemented with 5-10 gram doses of safflower seed extract every 2-3 hours combined with Jookyom in ginger tea. This regimen was maintained for about 12 days, and was modified slightly to provide higher doses four times daily for about another 30 days. The total weekly dose of safflower seed was about 1500 g and about 250 g of Jookyom. The patient was deemed cured at day 23 by his physician, in contrast to his pre-treatment recuperative estimate of about 1 year.

Improvement in children with bone disorders has been demonstrated after a course of therapy lasting about one week.

While certain preferred embodiments of the invention have been described herein in detail, numerous alternative embodiments are contemplated as falling within the scope of the invention. Consequently, the claims are not to be limited to the example provided herein.

What is claimed is:

1. A therapeutic composition comprising a mixture of safflower seed and bark of *ulmas davidiana* root, wherein said safflower seed comprises at least about 90 percent and said bark of *ulmas davidiana* root comprises no more than about 10 percent by weight of said composition.

2. A therapeutic composition comprising from about 50 to about 100 grams of a mixture containing about 90 to about 100 percent fried safflower seed and about 10 to about 0 percent bark of *ulmas davidiana* root.

3. A composition for the treatment of bone disorders in a mammal comprised of the aqueous extract of safflower seed.

* * * * *